US005741237A

United States Patent [19]

Walker

[11] Patent Number: 5,741,237

[45] Date of Patent: Apr. 21, 1998

[54] SYSTEM FOR DISPOSAL OF FLUIDS

[76] Inventor: Kenneth Gordon Walker, 109 - 549 Dansey, Coquitlam, Canada, V3K 3G1

[21] Appl. No.: 627,011

[22] Filed: Apr. 3, 1996

[30] Foreign Application Priority Data

| | | | |
|---|---|---|---|
| Apr. 10, 1995 | [CA] | Canada | 2146673 |
| Apr. 19, 1995 | [CA] | Canada | 2147292 |

[51] Int. Cl.$^{6}$ .................... A61M 1/00; B08B 3/00

[52] U.S. Cl. .................... 604/317; 604/320; 604/323; 604/322; 604/326; 134/50

[58] Field of Search .................... 604/317–326; 134/150, 166, 169, 50; 422/300, 302; 588/258, 900

[56] References Cited

U.S. PATENT DOCUMENTS

| | | | |
|---|---|---|---|
| 2,848,996 | 8/1958 | Kowal . | |
| 2,896,643 | 7/1959 | Ottoson . | |
| 3,678,955 | 7/1972 | Nelson . | |
| 3,833,417 | 9/1974 | Griparis | 134/22 |
| 3,916,924 | 11/1975 | McGowan | 134/95 |
| 4,039,351 | 8/1977 | Butler . | |
| 4,092,993 | 6/1978 | Stevenson . | |
| 4,106,155 | 8/1978 | Fosslien . | |
| 4,111,716 | 9/1978 | Stevenson . | |
| 4,119,114 | 10/1978 | Bolton et al. . | |
| 4,142,545 | 3/1979 | Billigmeier . | |
| 4,144,901 | 3/1979 | Stevenson . | |
| 4,344,469 | 8/1982 | Brown . | |
| 4,384,580 | 5/1983 | Leviton | 604/323 |
| 4,386,637 | 6/1983 | Buchanan et al. . | |
| 4,403,611 | 9/1983 | Babbit et al. . | |
| 4,452,268 | 6/1984 | Icking et al. . | |
| 4,673,006 | 6/1987 | Speck . | |
| 4,863,446 | 9/1989 | Parker | 604/317 |
| 4,957,491 | 9/1990 | Parker . | |
| 5,117,857 | 6/1992 | Smith . | |
| 5,185,007 | 2/1993 | Middaugh et al. | 604/323 |
| 5,242,434 | 9/1993 | Terry | 604/326 |
| 5,380,308 | 1/1995 | Gunya et al. | 604/323 |
| 5,449,009 | 9/1995 | Kerwin et al. | 134/50 |

*Primary Examiner*—John G. Weiss
*Assistant Examiner*—David J. Cho
*Attorney, Agent, or Firm*—Oyen, Wiggs, Green & Mutala

[57] ABSTRACT

A system for collecting and disposing of body fluids collected during surgery comprises a canister and a servicing unit for removing the body fluids from the canister and cleaning the canister for re-use. The canister is a vessel having sidewalls, a bottom and a lid. The lid has a first inlet port for the inflow of body fluids into the canister during surgery and a vacuum port for application of vacuum to the canister to induce the inflow of body fluids into the canister. The lid has a second inlet port for the inflow of cleaning fluid into the canister and a spray head in fluid communication with the second inlet port for spraying the cleaning fluid within the canister. The lid also has an outlet port with a suction tube extending into the canister for the outflow of body fluids and cleaning fluid from the canister. Caps are provided for closing those ports when the canister is being used to collect body fluids during surgery. The servicing unit has a first fluid conduit means to conduct fluid from the canister to a drain, and a second fluid conduit means to conduct cleaning fluid from a source of cleaning fluid to the second inlet port of the canister. There are connectors for connecting the first fluid conduit means to the outlet port of the canister and for connecting the second fluid conduit means to the second inlet port of the canister. Means are provided to control the flow of fluids through the fluid conduit means.

15 Claims, 6 Drawing Sheets

53
63
1

42
32
46
60
34
26
12
20
18
24
22
28
30
43
23
41
39
57
40
38
10
44
14
16

SYSTEM FOR DISPOSAL OF FLUIDS

FIELD OF THE INVENTION

The invention pertains to a system for disposing of fluids and in particular a system for the safe disposal of body fluids collected during surgical procedures.

BACKGROUND OF THE INVENTION

During surgery and other medical procedures, blood and other potentially infectious fluids are collected which must eventually be disposed of, without undue risk of infection to hospital workers by pathogens that may be present in the fluids. Disposable suction canisters, or disposable liners for canisters, are commonly used at present to collect fluids. These are either incinerated together with the collected fluids, or the fluids may be emptied to a drain by hospital workers and the empty canisters subsequently incinerated or removed to a remote location for disposal. Prior to incineration or disposal, disinfecting or gelling agents are often dispensed in the canisters. The additional handling of canisters required to carry out these procedures increases the likelihood of exposure to the collected body fluids and therefore increases the risk to workers of infection by pathogens in the fluids.

Reusable gravity fed fluid collection devices such as "kickbuckets" are also used in operating rooms, but such devices must typically be emptied and cleaned by hand, or disposable liners in such devices must be disposed of, again exposing workers to the risk of contact with the body fluids during handling. In the present application, all such devices are referred to as canisters.

Sophisticated fluid disposal systems have been described that use specialized collection containers that are washed for reuse, such as the device disclosed in U.S. Pat. No. 5,449,009 issued to Kerwin et al. on Sep. 12, 1995. Such units have the disadvantage that they are not adapted for use with standard canisters or with the operating room and hospital fixtures that are commonly adapted to fit standard canisters. Moreover, the ports of the Kerwin et al. Container must be open before the container can be placed in the apparatus for servicing. This gives rise to a risk of spilling the container contents and exposing the operator to risk of infection. The Kerwin et al. device also suffers from an important operational disadvantage. Hazardous fluids are removed from the collection container in Kerwin et al. by introduction of pressurized air into the collection container to displace the hazardous fluids. It will be appreciated that this approach entails some risk of rupturing the collection container and dispersing the hazardous fluids contained in it.

There is a need in the art to provide a system for disposing of body fluids which includes a reusable collection device and which permits disposal of the fluids and cleaning of the collection device for re-use without undue risk of exposure of hospital workers to pathogens in the fluids.

SUMMARY OF THE INVENTION

In accordance with a preferred embodiment of the invention, there is provided a system for collecting and disposing of body fluids collected during surgery comprising a canister and a servicing unit for removing the body fluids from the canister and cleaning the canister for re-use. The canister is a vessel having sidewalls, a bottom and a lid. The lid has a first inlet port for the inflow of body fluids into the canister during surgery and vacuum port for application of vacuum to the canister to induce the inflow of body fluids into the canister. The lid has a second inlet port for the inflow of cleaning fluid, such as a solution of detergent, into the canister and a spraying means in fluid communication with the second inlet port for spraying the cleaning fluid within the canister. The lid also has an outlet port with a suction tube extending into the canister for the outflow of body fluids and cleaning fluid from the canister. Means for closing the second inlet port and the outlet port are provided for closing those ports when the canister is being used to collect blood during surgery.

The servicing unit has a body with a compartment which contains the canister while it is being emptied and cleaned. The servicing unit has a first fluid conduit means to conduct fluid from the canister to a drain, with pump means to pump fluid through the first fluid conduit means. The servicing unit also has second fluid conduit means to conduct cleaning fluid from a source of cleaning fluid to the second inlet port of the canister. There are connector means for connecting the first fluid conduit means to the outlet port of the canister and for connecting the second fluid conduit means to the second inlet port of the canister. Means are provided to control the flow of fluids through the fluid conduit means.

The connector means of the servicing unit preferably comprises a connector head having first and second vertically displaceable connector tubes in fluid communication with the first and second conduit means respectively. Means for lowering and raising the connector tubes are provided for connecting them to and disconnecting them from the mating ports on the canister lid.

According to another embodiment of the invention, the servicing unit is a portable unit in which the fluid conduit means extend from the body of the servicing unit and terminate in a connector head adapted to be held in an operator's hand and to connect to a canister. Alternatively, the servicing unit may be mounted on a countertop, with most of its plumbing fixtures contained beneath the countertop.

The built-in spray nozzles and suction tube of the canister avoids any requirement to open the canister in order to empty and disinfect it, apart from simply uncapping the ports of the canister.

BRIEF DESCRIPTION OF THE DRAWINGS

In drawings which illustrate embodiments of the invention.

DETAILED DESCRIPTION OF THE INVENTION

A system for disposal of body fluids collected during surgery comprises a canister which acts as a collection device and a servicing unit for emptying the fluids from the canister and cleaning the canister for re-use.

Figure 1:
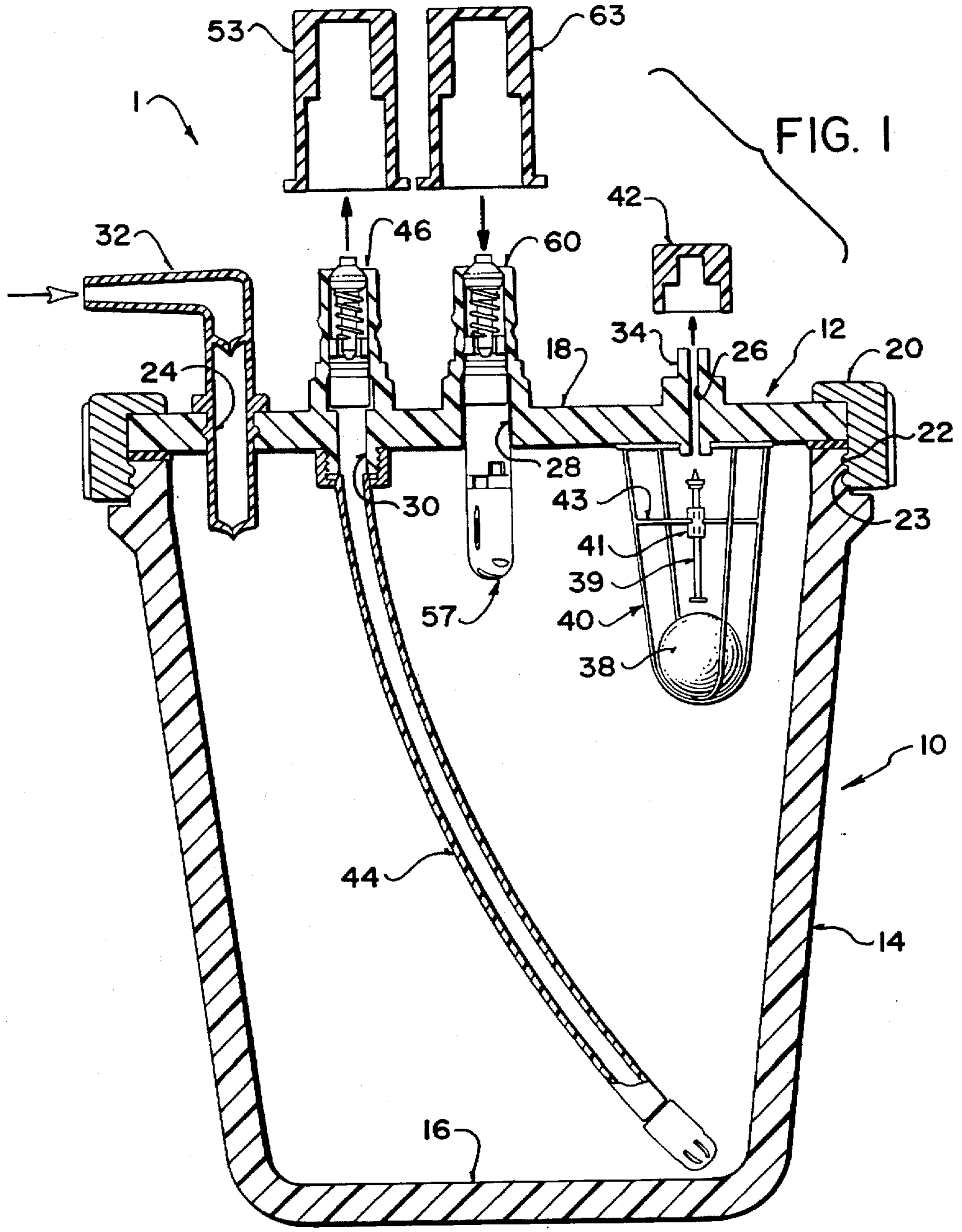
FIG. 1 is a vertical cross-section view of the canister.

Referring to FIG. 1, which illustrates a first embodiment of the canister, the canister 1 has a body 10 and lid 12. Body 10 has sidewalls 14 and a substantially flat bottom 16. Lid 12 has a generally flat top 18 and circumferential rim 20 with threads 22 which engage mating threads 23 on the upper lip of the body 10 to affix and seal lid 12 to body 10, a gasket may be provided to assist in sealing engagement of lid 12 to body 10.

Lid 12 may have four openings therein which extend into canister 1, two of which are used for the collection of body fluids during surgery, namely fluid inlet port 24 and vacuum port 26; and two of which are used for emptying and cleaning of the canister, namely inlet port 28 and outlet port 30. Gravity fed "kickbuckets" are also commonly used for fluid collection. Gravity fed canisters will generally lack a vacuum port. It will be appreciated that ports 24, 26, 28, 30 in lid 12 may be positioned in a wide variety of ways relative to one another. Similarly, lid 12 may be provided with other ports for use in a variety of applications.

Inlet port 24 has inlet tube 32 fitted therein, adapted to connect to a conduit to conduct body fluids to the canister during surgery. Inlet tube 32 is provided with one-way valves to inhibit reverse flow of body fluids. Inlet tube 32 may be removably attached to inlet port 24 and may be disposable. Vacuum port 26 is fitted with a nipple 34 extending vertically outward therefrom and adapted to connect to a vacuum conduit. A check valve to prevent overflow of body fluid from vacuum port 26 is provided, consisting of floatball 38 and needle valve 39. Needle valve 39 is slidably retained in guide sleeve 41 supported by radial arms 43 of floatball cage 40. In an alternative embodiment (not shown), a vacuum port check valve may consist of a seat extending inwardly from vacuum port 26, the seat being adapted for sealing engagement with a floatball. It will be appreciated that a variety of vacuum port check valve designs are possible, preferable designs have a minimal surface area and profile to lessen interference with the cleaning process. During the collection of body fluids, when the fluid level in the canister 1 becomes sufficiently high, floatball 38 is floated upward against needle valve 39, stopping the application of vacuum to canister 1 and thus stopping the flow of further fluid into inlet port 24. Cap 42 fits over nipple 34 to seal vacuum port 26 when the vacuum conduit is removed from nipple 34, to seal the vacuum port 26 and prevent spillage of fluid through it. Vacuum port 26 may be fitted with a filter (not shown) to inhibit the passage of liquid through it.

Outlet port 30 extends through lid 12. Suction tube 44 is fitted to the inner end of port 30, extending into canister 1 and terminating in a strainer end adjacent bottom wall 16. Suction tube 44 and the strainer end may be disposable. Nipple 46 extends outwardly from port 30 and is adapted to be connected to the servicing unit, as described below. Nipple 46 may be fitted with a check valve, in the form of a standard hydraulic quick-connector. Cap 53 may be used to seal nipple 46 when port 30 is not in use. In the embodiment shown in FIG. 3, cylindrical wall 48 extends upward from top 18 concentrically with nipple 46 and is adapted to receive cap 53.

Figure 3:
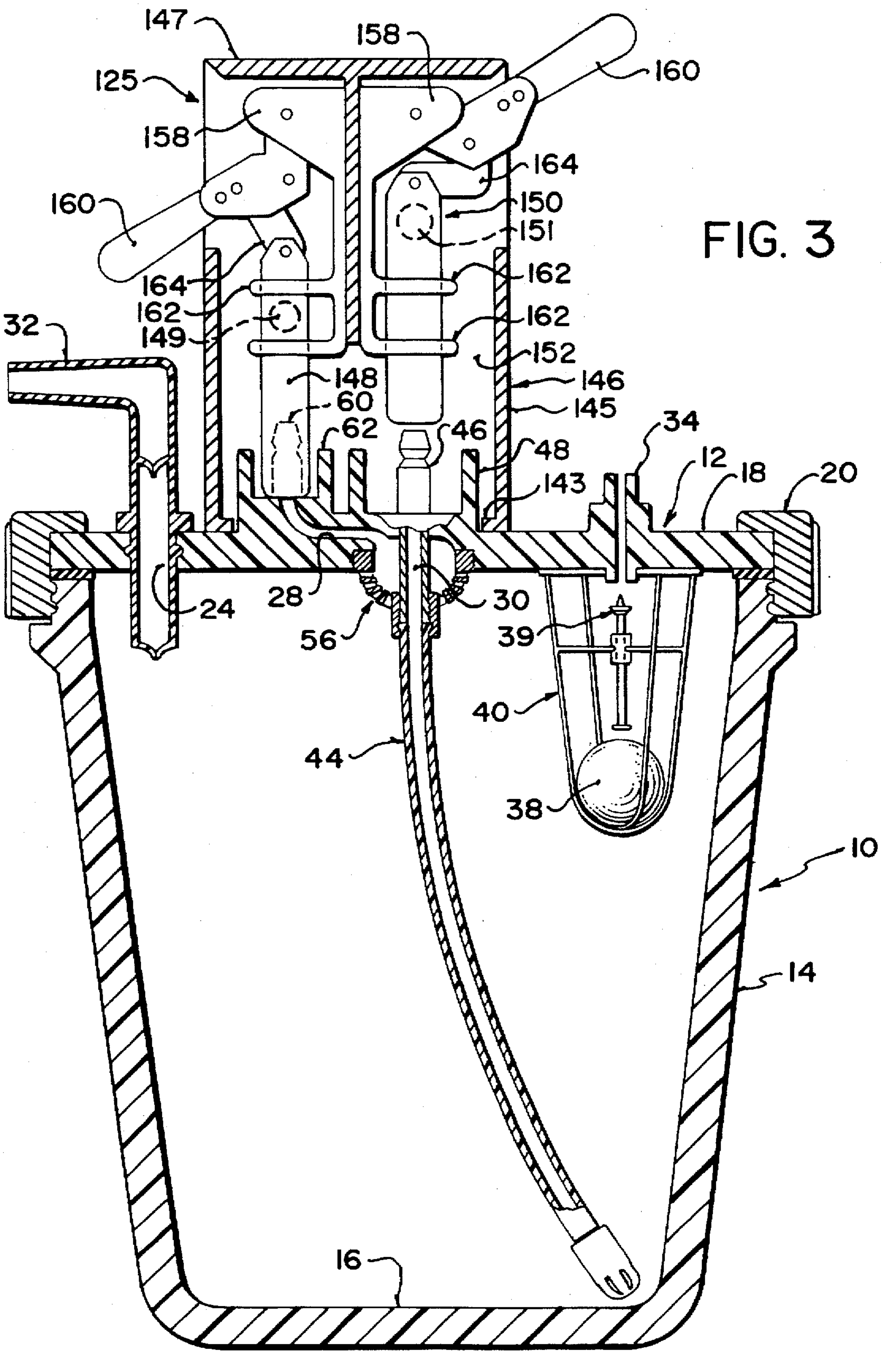
FIG. 3 is a vertical cross-section view of an alternative embodiment of the canister and of a manual embodiment of the connector head of the servicing unit.

Nipple 60 is connected through port 28 in lid 12 to rotatable sprayhead 57. Sprayhead 57 has orifices disposed thereon and is adapted to spray cleaning fluid flowing into canister 1 against the interior parts of the canister. Sprayhead 57 may be a rotatable nozzle similar in design to compact keg washing nozzles available from Spraying Systems Co. of Wheaton, Ill., with orifices disposed to actuate rotation of sprayhead 57 and provide an appropriate dispersal of fluid in canister 1. In FIG. 3, sprayhead 56 is in the form of an annulus around suction tube 44. Nipple 60 may be fitted with a check valve, as in a standard hydraulic quick-connector, and is adapted to connect to servicing unit 100, as described below. Cap 63 may be used to seal nipple 60 when it is not in use. In FIG. 3, cylindrical wall 62 extends upward from top surface 18 concentrically with nipple 60 and is adapted to receive cap 63.

When canister 1 is being used for collecting body fluids during surgery, caps 63 and 53 may be put in place to seal nipples 60 and 46, a vacuum conduit is connected to nipple 34 and a body fluid inflow conduit is connected to inlet tube 32. Vacuum is applied through the vacuum conduit, inducing the flow of body fluids into the canister, in which they are collected. When the canister is full, it can be disconnected from the vacuum conduit and body fluid inflow conduit and cap 42 placed over nipple 34. The canister is then ready to be emptied and cleaned in servicing unit 100, as described below.

Figure 2:
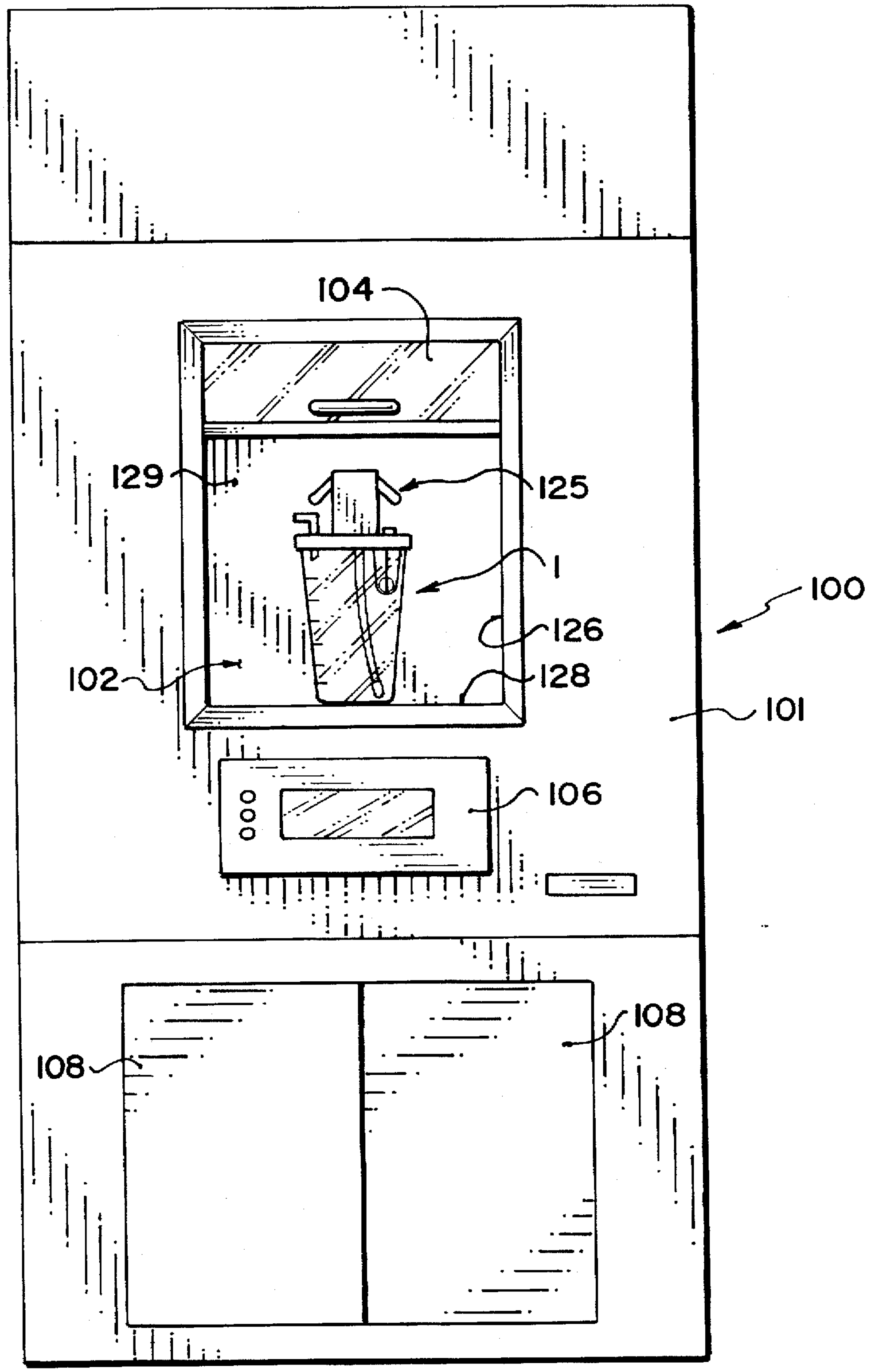
FIG. 2 is a front elevation view of the servicing unit holding a canister.

Referring to FIG. 2, servicing unit 100 is a generally rectangular apparatus having an outer wall 101 and a receiving compartment 102 in which canister 1 is placed for servicing, i.e. for removal of the collected body fluids and cleaning of the canister.

Receiving compartment 102 is open at the front of the servicing unit for access. It has a transparent door 104 which may slide downwards to cover the opening for worker protection during servicing of canister 1. Many canisters are also transparent by design. The operator is therefore able to visually observe the progress of the emptying and cleaning of the canister. Receiving compartment 102 preferably has an interior light to aid in this visual assessment. Control video display panel 106 on the front of the servicing unit contains the controls for operating the unit. A storage compartment is provided in the bottom part of the servicing unit, with access doors 108 which open at the front of the unit, for convenient storage of drums of detergent.

The receiving compartment 102 can optionally have a bracket or holding device on the floor 128 for holding canister 1. Alternatively, floor 128 may be provided with stepped concentric circular indentations to accommodate and position canisters of various dimensions beneath connector unit 125. An indented keyway may also be provide to mate with an asymmetrical feature near the bottom of a canister to properly orient the canister for engagement with connector unit 125.

In an alternative embodiment, the servicing unit is a portable unit comprising a body that can be moved by means of castors. The body may have a hose extending therefrom with a connector head at the end thereof, the hose containing a cleaning fluid conduit and an fluid outlet conduit. Connector tubes may be provided that are adapted to connect to and provide fluid communication with a canister, as described below. The body of the portable servicing unit may contain a cleaning fluid circuit to deliver wash water through cleaning fluid conduit and a fluid outflow circuit to evacuate body fluids through the fluid outlet conduit. The portable servicing unit may have electronic controls, as described below for the stationary embodiment of the servicing unit. A hose fitting may be provided to connect the portable servicing unit to a source of pressurized water.

A manual embodiment of connector unit 125 and its manner of attachment to an alternative embodiment of a canister are illustrated in FIG. 3. Connection unit 125 can be raised or lowered according to the height of the canister to be serviced. Connection unit 125 is located inside receiving compartment 102 and is mounted on a vertically-sliding track (shown schematically in FIG. 4) positioned immediately behind rear wall 129 of receiving compartment 102. The connector unit 125 extends forward horizontally from the rear wall 129. The connector unit 125 is divided longitudinally into two sections, one of which carries a cleaning fluid supply conduit (not shown) and one of which carries an outflow conduit (not shown).

Referring to FIG. 3, the connector head 125 has a housing 146 comprising top wall 147, bottom wall 143, back wall 152, side walls 145 and a removable front wall (not shown). Housing 146 contains and supports connector tubes 148, 150, which are adapted to fit over and form a sealed fluid connection with nipples 60 and 46 respectively of the canister. Connector tube 148 includes port 149 for fluid communication with the cleaning fluid supply conduit (not shown). Connector tube 150 includes port 151 for fluid communication with the outflow conduit (not shown). Connector tubes 148, 150 have vertical bores therethrough (not shown) extending from the bottom end thereof to ports 149, 151. The bores of the connector tubes are sized to fit snugly over nipples 60, 46 to provide a good fluid seal. Connector tubes 148, 150 may house quick connector couplers (not shown) having check valves (not shown) to prevent leaks.

When connector unit 125 is lowered into position for servicing canister 14, bottom wall 143 of housing 146, abuts the upper surface of canister lid 12, proximate cylindrical walls 48 and 62. Housing 146 of the connector unit 125 substantially surrounds connector tubes 148, 150 and may act as a shield if a leak should occur to contain any leaking spray.

Two brackets 158 are affixed to a vertical flange depending downwardly from top wall 147. Each bracket has two horizontally-disposed semi-circular tines 162 which hold connector tubes 148, 150 and permit vertical movement of the connector tubes therethrough without obstructing ports 149, 151. Connector tubes 148, 150 are connected to the brackets by means of an assembly which enables the connector tubes to be manually raised and lowered for connection to the canister and to be held firmly in both the raised and lowered positions. Each bracket 158 has a clamp handle 160 pivotally attached thereto. An arm 164 is pivotally connected to each handle and pivotally connected to the upper end of a connector tube 148, 150 such that the manual raising and lowering of a clamp handle 160 by an operator raises and lowers a connector tube 148, 150. It will be apparent that in lieu of this manually-operated mechanism, a pneumatic or hydraulic mechanism can be provided, as is illustrated schematically in FIG. 4.

Figure 4:
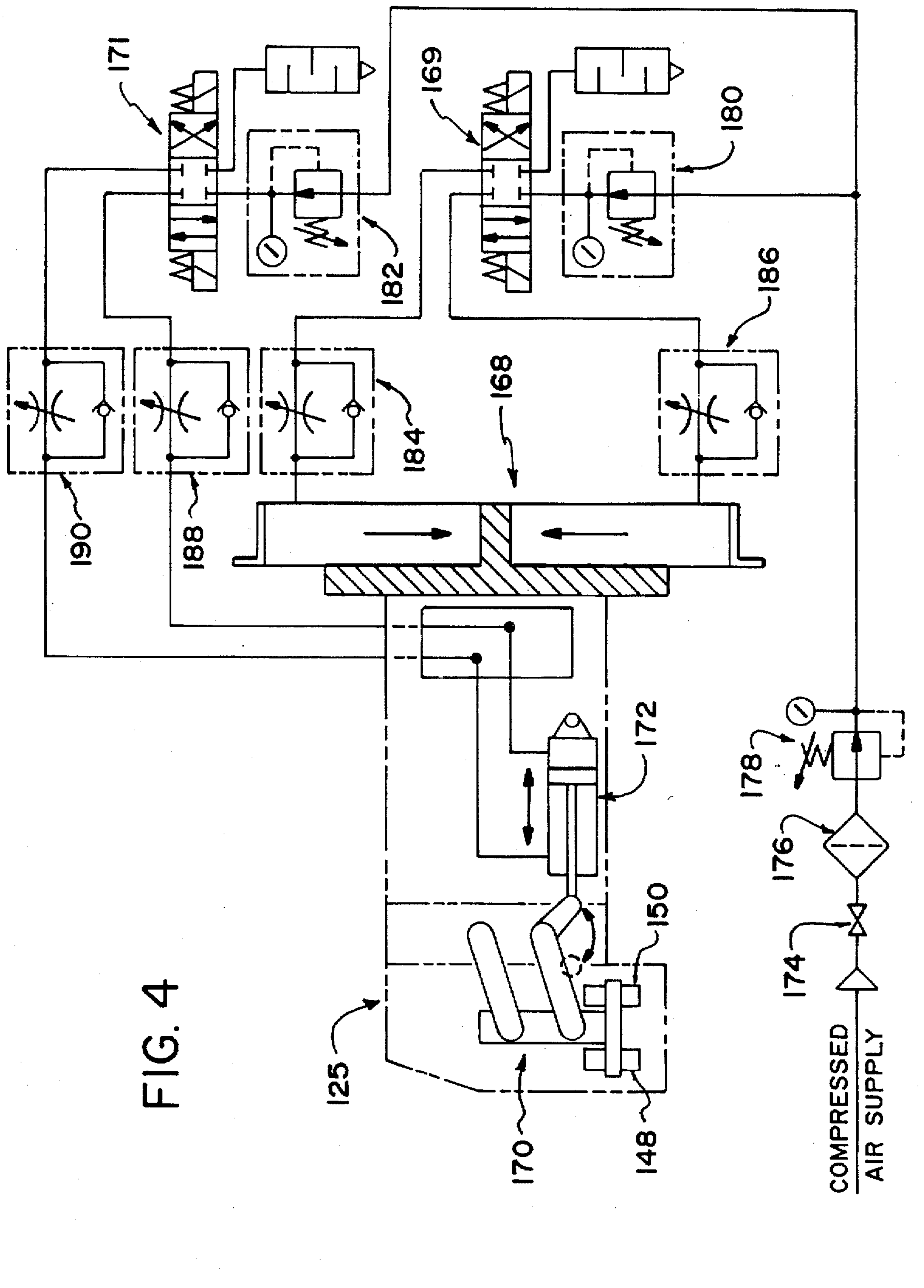
FIG. 4 is a schematic view showing an alternative embodiment of the connector head of the servicing unit with pneumatic and mechanical actuators.

Referring to FIG. 4, connector unit 125 is mounted on a pneumatic vertical lift assembly 168, such as a mechanical joint band cylinder. Connector tubes 148, 150 are mounted for vertical displacement on a line swing connection assembly 170. The line swing connection assembly is actuated by a pneumatic swing connection cylinder 172. The displacement of the vertical lift assembly 168 and the line swing assembly 170 are controlled by separate control valves 169 and 171 respectively, which receive a compressed air supply through a shut-off valve 174, filter 176 and pressure regulators 178, 180, 182. One set of flow control valves 184, 186 regulates actuation of the vertical lift assembly 168, another set of flow control valves 188, 190 regulates actuation of the line swing assembly 172.

Figure 5:
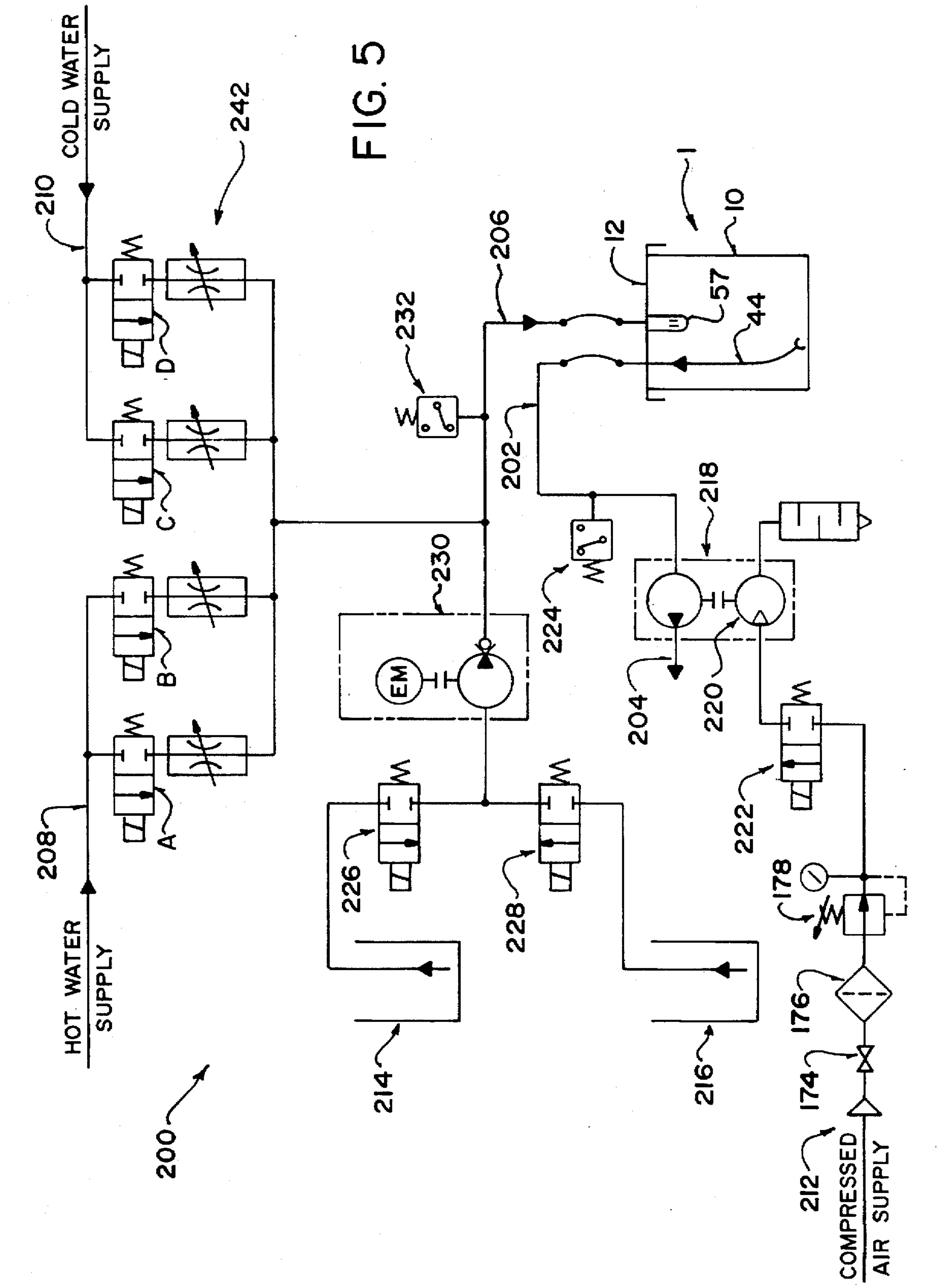
FIG. 5 is a schematic view of the fluid handling system of the servicing unit.

Referring to schematic FIG. 5, the fluid handling system 200 of the servicing unit 100 comprises first fluid conduit means to conduct fluid from canister 1 to a drain 204 and second fluid conduit means 206 to conduct cleaning fluid or water to the inlet port on the canister. The unit may be connected to pressurized hot and cold water supply lines 208, 210, a drain 204 and a compressed air supply 212. The unit is provided with a detergent and water reservoir 214 and a disinfectant reservoir 216.

First fluid conduit 202 means comprises a vacuum pump 218 connectable to suction tube 44. The vacuum pump is powered by an air motor 220. The air motor is actuated by energizing solenoid actuated pneumatic valve 222. Vacuum switch 224 senses any vacuum in the suction line, indicating that liquid is being removed from canister 1. The vacuum pump may discharge liquid to a sanitary drain 204 or other fluid discharge means (such as a sanitizing treatment). In an alternative embodiment, the vacuum pump may be a peristaltic pump or another pump adapted for use with viscous fluids. This type of pumping action may help to break up clots or congealed material drawn from the canister, and also eliminates contact of the potentially infectious fluids with the moving parts of the pump.

Second fluid conduit means comprises means 206 for supplying water, a detergent and water mixture or a disinfectant solution. A detergent and water mixture is stored in a first reservoir 214. A disinfectant solution is stored in a second reservoir 216. The reservoirs may be provided with level sensors (not shown) to provide an indication when a reservoir needs to be refilled. Solenoid actuation of two-way valve 226 permits flow from the first reservoir 214. Solenoid actuation of two-way valve 226 permits flow from the second reservoir 216. Fluid flow from the reservoirs is induced by a metering pump 230. A pressure switch 232 on the spray line indicates when the metering pump is primed. The metering pump is preferably capable of delivering fluid through the spray line 206 in repeated bursts of pressure, to help dislodge dried or congealed material in the canister.

Figure 6:
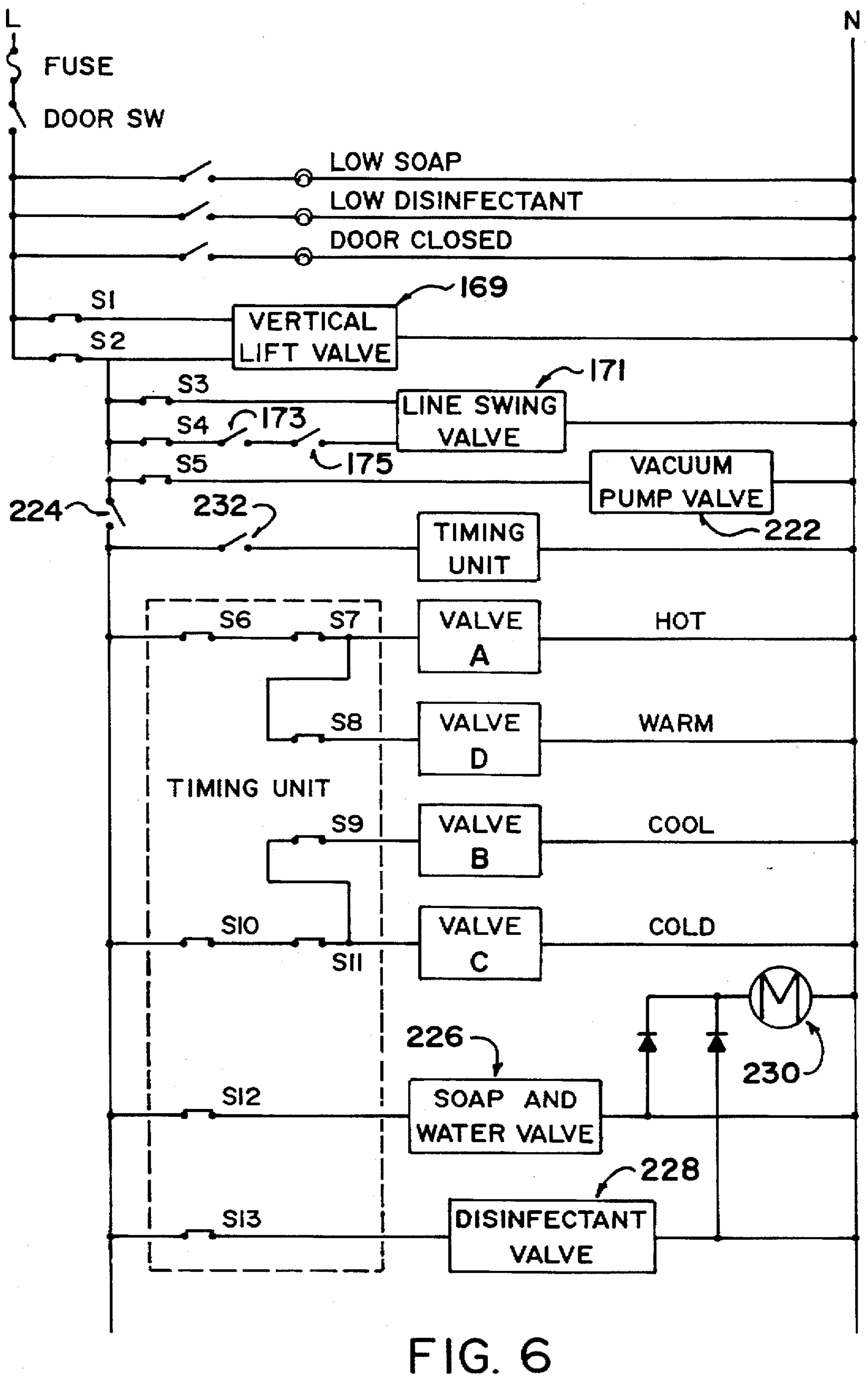
FIG. 6 is a schematic view of the electronic control system of the servicing unit.

Referring to FIG. 6 and as illustrated in the Truth Table shown below, water supply control valves A, B, C, D and associated flow controllers 242 may be used to regulate the temperature of water delivered to the canister.

TRUTH TABLE

| FUNCTION | S1 | S2 | S3 | S4 | S5 | S6 | S7 | S8 | S9 | S10 | S11 | S12 | S13 |
|---|---|---|---|---|---|---|---|---|---|---|---|---|---|
| CONNECT CONTAINER | O | C | O | C | O | O | O | O | O | O | O | O | O |
| START VACUUM | O | C | O | C | C | O | O | O | O | O | O | O | O |
| RUN HOT WATER | O | C | O | C | C | C | C | O | O | O | O | O | O |
| RUN WARM WATER | O | C | O | C | C | C | C | C | O | O | O | O | O |
| RUN COOL WATER | O | C | O | C | C | O | O | O | C | C | C | O | O |
| RUN COLD WATER | O | C | O | C | C | O | O | O | O | C | C | O | O |
| SOAP AND WATER | O | C | O | C | C | O | O | O | O | O | O | C | O |
| RUN DISINFECTANT | O | C | O | C | C | O | O | O | O | O | O | O | C |
| DISCONNECT CONTAINER | C | O | C | O | O | O | O | O | O | O | O | O | O |

O = OPEN
C = CLOSED

Valve A is energized to supply hot water. Valve C is energized to supply cold water. Valves A and D are energized to supply warm water. Valves B and C are energized to supply cool water. Flow controllers 242 may be adjusted to set desired temperatures more precisely.

The rate of evacuation of fluid from the canister by the vacuum pump may advantageously be equal to or greater than the rate of pumping cleaning fluid into the canister by the metering pump. In this way, rinsing and flushing of the canister is continuous, minimizing pooling of cleaning fluid in the bottom of the canister.

As shown in electrical schematic FIG. 6, controls may be provided for the various functions of the servicing unit. Conventional electrical controls, such as programmable electronic controls, of types well known to persons skilled in the art are provided to control (a) the actuation and speed of pumps; (b) the actuation, speed and direction of motors; (c) the opening and closing of valves; and (d) indicators to provide information to operators on control video display panel 106. Liquid level sensors for each of the reservoirs may be used to send signals to the control video display panel if fluid levels are low and require replenishment. Switches may also be included that ensures the transparent door is closed before any operations of the servicing cycle may commence, or that the connector unit 125 is securely attached to the canister 1, or to shut off the metering pump and water valves if the vacuum pump ceases to function.

A suitable controller for the apparatus is the Sysmac CQM 1 Series Programmable Controller sold by Omron Electronics of Schaumburg, Ill. A suitable control panel 106 is the NT Series Touch Screen also sold by Omron Electronics.

To use the servicing unit, the operator enters the type and capacity of the canister to be serviced on control panel 106 by selecting one of several pre-set cycles that are displayed. A signal is sent from the programmable controller to the vacuum pump and to the flow controllers to adjust vacuum and washing fluid pressure settings appropriately to suit the canister's capacity. The operator places canister 1 in receiving compartment 102, positions it under the connector unit and removes caps 63 and 53 from lid 12 to expose quick-connect ends 46 and 60. Cap 42 is placed over nipple 34 to close vacuum port 26. Inlet tube 32 is left open as an air vent. The operator closes compartment door 104 and selects "connect" on control panel 106. A signal is sent from the controller to the vertical lift assembly 168 that lowers the connector unit 125 over the canister lid 12. Limit switches 175 detect that the arm has reached the canister, arresting further travel of the vertical lift assembly. Limit switches or proximity sensors 173 may also verify that the quick-connect ends 46, 60 of the canister are in proper position. When this is verified, the swing connection cylinder 172 actuates the line swing assembly 170, mating couplers (not shown) in cylinders 148, 150 to nipples 46, 60 on canister 1.

The canister is now ready to be emptied and cleaned and an indicator will display this information on the control panel. The operator chooses "start cycle" on the panel and a signal is sent to valve 222 actuating the air motor 220 of the vacuum pump 218. At all stages of cleaning, the vacuum pump is running. Vacuum switch 224 senses vacuum in the suction line 202. The liquid contents of the canister are withdrawn through suction tube 44 and disposed of, typically to a sanitary sewer.

When the canister has been emptied, a condition which may be indicated by manual input by an operator, a preliminary cool water rinse is initiated. A signal sent from the controller energizes solenoid valves B and C allowing cool water to flow into the canister. The cool rinse water is evacuated continuously out suction tube 44. After approximately one minute, water valves B and C are de-energized and valve 226 opens and the metering pump 230 begins drawing a detergent and water mixture from the first reservoir 214 and delivers this mixture to canister 1. The pressure switch 232 will verify that the metering pump is primed. If the pressure switch reads "zero", then the timing cycle is delayed until the pump is primed. The detergent and water mixture may be sprayed inside the canister for approximately 3–4 minutes, and this fluid is also continuously evacuated out suction tube 44. When this portion of the cycle is complete, valve 226 is de-energized and valve 228 opens. The metering pump then draws disinfectant from the second reservoir 216 and it may be sprayed inside the canister for approximately 3 minutes. Valve 228 is then de-energized and water valve A is energized. A final hot water rinse of approximately 2 minutes completes the cycle. Inlet tube 32 may be disposed of following the final rinse. The canister may also be washed again in a conventional washer following decontamination in the service unit.

Throughout the cleaning cycle, the vacuum switch 224 will monitor and verify that the vacuum pump 218 is running. When the cycle is complete, water valves A, B, C, D will de-energize and the vacuum pump 218 will continue to run for several seconds to evacuate remaining rinse water. When the vacuum pump has shut off, this will be indicated on control panel 106. The operator may visually verify that canister 1 is clean; if it is, the operator may select "disconnect" on the control panel. When "disconnect" is selected, a signal is sent to the swing connection cylinder 172 de-actuating the line swing connection assembly 170, un-coupling cylinders 148, 150 of connector unit 125 from canister 1. A signal is sent to the vertical lift assembly 168 to raise the connector unit 125. The operator may then open transparent door 104 and remove canister 1 which has been emptied, rinsed and decontaminated. Servicing unit 100 is then ready to receive another canister.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A system for collecting and disposing of body fluids comprising:

(a) a canister for receiving said body fluids, comprising:

a body having side walls and a bottom and adapted to sealably receive a removable lid;

a removable lid for sealably covering said body;

a first inlet port in said lid for inflow of body fluids into said canister;

a second inlet port in said lid for inflow of cleaning fluid into said canister;

spraying means in fluid communication with said second inlet port for spraying said cleaning fluid within said canister;

means for closing said second inlet port during said inflow of body fluids into said canister;

an outlet port in said lid for sectioning body fluids and said cleaning fluid from said canister;

a removable suction tube in fluid communication with said outlet port and extending to said bottom of said canister;

means for closing said outlet port during said inflow of body fluids into said canister;

a vacuum port in said lid for application of vacuum to said canister for inducing said inflow of body fluids into said canister; and, a check valve on said lid operably coupled to said vacuum port for stopping the inflow of body fluids into said canister when the level of body fluids in said canister reaches a predetermined level;

(b) a servicing unit for removing said body fluids from said canister and cleaning said canister, comprising:
first fluid conduit means to conduct fluid in said canister to a drain;
second fluid conduit means to conduct cleaning fluid from a source of said cleaning fluid to said second inlet port;
connector means for detachably connecting said first fluid conduit means to said outlet port of said canister and for detachably connecting said second fluid conduit means to said second inlet port of said canister;
suction means to induce a flow of fluid from said suction tube in said canister through said first fluid conduit means; and
means to induce a flow of cleaning fluid to said canister through said second fluid conduit means.

2. The system in accordance with claim 1 wherein said servicing unit further comprises a container for detergent in fluid communication with said second fluid conduit means, and means for introducing said detergent in said container into said second fluid conduit means.

3. The system in accordance with claim 1 wherein said suction means to induce a flow of fluid from said suction tube in said canister through said first fluid conduit means is a pump.

4. The system in accordance with claim 1 further including means for closing said vacuum port of said canister.

5. The system in accordance with claim 1 wherein said check valve comprises a floatball operably coupled to a needle valve.

6. The system in accordance with claim 5 further comprising a floatball cage for housing said floatball, said floatball cage comprising a needle valve guide for slidably retaining said needle valve.

7. The system in accordance with claim 1 wherein said spraying means is a rotatable sprayhead.

8. The system in accordance with claim 1 wherein said second fluid conduit means comprises a pump capable of providing pulses of fluid pressure.

9. The system in accordance with claim 1 wherein said spraying means is a sprayhead forming an annulus around said suction tube.

10. A system for collecting and disposing of body fluids comprising:

a canister for receiving said body fluids, comprising:
a body having side walls and a bottom and adapted to receive a lid;
a lid for covering said body;
a first inlet port in said lid for inflow of body fluids into said canister;
a second inlet port in said lid for inflow of cleaning fluid into said canister;
spraying means in fluid communication with said second inlet port for spraying said cleaning fluid within said canister;
means for closing said second inlet port during said inflow of body fluids into said canister;
an outlet port in said lid for outflow of body fluids and said cleaning fluid from said canister;
a conduit in fluid communication with said outlet port extending into said canister; and
means for closing said outlet port during said inflow of body fluids into said canister;

(b) a servicing unit for removing said body fluids from said canister and cleaning said canister, comprising:
a body adapted to receive said canister;
first fluid conduit means to conduct fluid in said canister to a drain;
second fluid conduit means to conduct cleaning fluid from a source of said cleaning fluid to said second inlet port;
connector means for detachably connecting said first fluid conduit means to said outlet port of said canister and for detachably connecting said second fluid conduit means to said second inlet port of said canister, wherein said connector means comprises a connector head having first and second connector tubes in fluid communication with said first and second conduit means respectively and means for moving said first and second connector tubes for connection to and disconnection from said outlet port and said second inlet port respectively;
means to induce a flow of fluid from said canister through said first fluid conduit means; and
means to induce a flow of cleaning fluid to said canister through said second fluid conduit means.

11. A system for collecting and disposing of body fluids, comprising:

(a) a canister for receiving said body fluids comprising:
a body having side walls and a bottom and adapted to receive a lid;
a lid for covering said body;
a first inlet port in said lid for inflow of body fluids into said canister;
a second inlet port in said lid for inflow of cleaning fluid into said canister;
spraying means in fluid communication with said second inlet port for spraying said cleaning fluid within said canister;
means for closing said second inlet port during said inflow of body fluids into said canister;
an outlet port in said lid for outflow of body fluids and said cleaning fluid from said canister;
a conduit in fluid communication with said outlet port extending into said canister; and
means for closing said outlet port during said inflow of body fluids into said canister; and (b) an apparatus for removing body fluids from said canister and cleaning said canister, comprising:
first fluid conduit means to conduct fluid in said canister to a drain;
second fluid conduit means to conduct cleaning fluid from a source of said cleaning fluid to an inlet port in said canister; and
a connector head having first and second connector tubes in fluid communication with said first and second fluid conduit means respectively and means for moving said first and second connector tubes for connection to and disconnection from said outlet port and said inlet port respectively.

12. A canister for receiving body fluids, said canister comprising:

(a) a body having side walls and a bottom and adapted to sealably receive a removable lid;
(b) a removable lid for sealably covering said body;
(c) a first inlet port in said lid for inflow of body fluids into said canister;
(d) a second inlet port in said lid for inflow of cleaning fluid into said canister;

(e) spraying means in fluid communication with said second inlet port for spraying said cleaning fluid within said canister;

(f) means for closing said second inlet port during said inflow of body fluids into said canister;

(g) an outlet port in said lid for suctioning body fluids and said cleaning fluid from said canister;

(h) a removable suction tube in fluid communication with said outlet port and extending to said bottom of said canister;

(i) means for closing said outlet port during said inflow of body fluids into said canister;

(j) a vacuum port in said lid for application of vacuum to said canister for inducing said inflow of body fluids into said canister: and, (k) a check valve on said lid operably coupled to said vacuum port for stopping the inflow of body fluids into said canister when the level of body fluids in said canister reaches a predetermined level.

13. The canister of claim 12 wherein said check valve is adapted to stop the inflow of body fluids into said canister when the level of body fluids in said canister reaches a level below the level of said spraying means.

14. A system for collecting and disposing of body fluids comprising:

(a) a canister as defined in claim 12;

(b) a portable servicing unit for removing body fluids from said canister and cleaning said canister for re-use comprising:

a body adapted for movement across a floor;

a first fluid conduit means to conduct fluid in said canister to a drain;

second fluid conduit means to conduct cleaning fluid from a source of said cleaning fluid to said second inlet port;

said first and second fluid conduit means extending from said body and terminating in a connector head adapted to connect said first fluid conduit means to said outlet port of said canister and to connect said second fluid conduit means to said second inlet port of said canister;

means to induce a flow of fluid from said canister through said first fluid conduit means; and means to induce a flow of cleaning fluid to said canister through said second fluid conduit means.

15. The system of claim 14 wherein said connector head is adapted to be held in an operator's hand.

* * * * *